United States Patent
Fortman et al.

(10) Patent No.: US 10,093,619 B2
(45) Date of Patent: Oct. 9, 2018

(54) MANUFACTURE OF ORGANOPOLYSULFIDES AND SALTS THEREOF

(71) Applicant: Arkema Inc., King of Prussia, PA (US)

(72) Inventors: George C. Fortman, Conshohocken, PA (US); Gary S. Smith, Collegeville, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 15/571,077

(22) PCT Filed: Apr. 29, 2016

(86) PCT No.: PCT/US2016/029929
§ 371 (c)(1),
(2) Date: Nov. 1, 2017

(87) PCT Pub. No.: WO2016/182759
PCT Pub. Date: Nov. 17, 2016

(65) Prior Publication Data
US 2018/0162810 A1  Jun. 14, 2018

Related U.S. Application Data

(60) Provisional application No. 62/158,690, filed on May 8, 2015.

(51) Int. Cl.
| | |
|---|---|
| *C01B 17/20* | (2006.01) |
| *C07C 319/24* | (2006.01) |
| *C07C 321/04* | (2006.01) |
| *C07C 321/08* | (2006.01) |
| *C07C 323/12* | (2006.01) |
| *H01M 10/052* | (2010.01) |
| *C07D 285/125* | (2006.01) |
| *H01M 10/0566* | (2010.01) |

(52) U.S. Cl.
CPC ............ *C07C 319/24* (2013.01); *C01B 17/20* (2013.01); *C07D 285/125* (2013.01); *H01M 10/052* (2013.01); *H01M 10/0566* (2013.01); *H01M 2300/002* (2013.01)

(58) Field of Classification Search
CPC .... C07C 319/24; C07D 285/125; C01B 17/20
See application file for complete search history.

(56) References Cited

U.S. PATENT DOCUMENTS

| | | | | |
|---|---|---|---|---|
| 3,022,351 | A * | 2/1962 | Mihm | C07C 319/24 |
| | | | | 568/26 |
| 3,392,201 | A * | 7/1968 | Warner | C07C 319/24 |
| | | | | 568/26 |
| 4,564,709 | A * | 1/1986 | Koyama | C07C 319/24 |
| | | | | 568/26 |
| 4,937,385 | A | 6/1990 | Buchholz et al. | |
| 5,442,123 | A * | 8/1995 | Arretz | C07C 319/24 |
| | | | | 568/22 |
| 5,530,163 | A | 6/1996 | Shaw | |
| 2014/0046097 | A1* | 2/2014 | Klobes | C08G 75/14 |
| | | | | 568/22 |
| 2015/0118140 | A1 | 4/2015 | Schmitt et al. | |
| 2015/0118535 | A1* | 4/2015 | Smith | H01M 10/0565 |
| | | | | 429/101 |
| 2017/0084953 | A1* | 3/2017 | Smith | H01M 10/0567 |

* cited by examiner

*Primary Examiner* — Amanda L Aguirre
(74) *Attorney, Agent, or Firm* — Steven D. Boyd

(57) ABSTRACT

A method of producing an organopolysulfide or salt thereof is provided which includes a step of mixing an organomonosulfide or salt thereof and elemental sulfur, wherein the mixing is carried out at a temperature not greater than 95 C and in the absence of any added liquid phase for a time effective to produce the organopolysulfide or salt thereof. The described method makes possible the preparation of organopolysulfides and organopolysulfide salts without the use of solvent or catalyst.

19 Claims, No Drawings

MANUFACTURE OF ORGANOPOLYSULFIDES AND SALTS THEREOF

This present application is the national phase under 35 USC § 371 of prior PCT International Application Number PCT/US2016/029929 filed Apr. 29, 2016 which designated the United States of America and claimed priority to U.S. Provisional Patent Application Ser. No. 62/158,690 filed May 8, 2015.

FIELD OF THE INVENTION

The present invention relates to processes useful for preparing organopolysulfides and salts thereof, including processes which do not require the use of solvent and/or catalyst and which may be carried out at relatively low temperatures.

DESCRIPTION OF THE RELATED ART

Organopolysulfides include polysulfides containing at least one organic group, such as a hydrocarbon group, bonded to a first sulfur atom of a polysulfide chain ($—S_n—$, where n is an integer greater than 1), wherein the terminal sulfur atom of the polysulfide chain is substituted with a hydrogen atom (to provide a thiol, —S—H). Such polysulfides may also be referred to as organopolythiols. Salts of such organopolysulfides are also known, wherein the hydrogen atom of the terminal thiol group is replaced with a cationic species such as $Li^+$. Such compounds may also be referred to as organopolythiolates. The cationic portion of the salt may be an alkali metal cation, alkaline earth metal cation, other metal cation, ammonium (e.g., quaternary ammonium) or phosphonium (e.g., quaternary phosphonium) or the like. Such organopolysulfides and organopolysulfide salts are known to be useful materials for a variety of applications, including, for example, as components of batteries (see WO 2013/155038, the disclosure of which is incorporated herein by reference in its entirety for all purposes). Accordingly, the development of practical, efficient methods for manufacturing organopolysulfides and salts of organopolysulfides would be of great commercial interest. In particular, synthetic processes that avoid the need to use high temperatures, solvents and/or catalysts, which generally add to production costs, would be desirable.

SUMMARY OF THE INVENTION

One aspect of the invention provides a method of producing an organopolysulfide and/or salt thereof, wherein the method comprises a step of mixing an organomonosulfide (and/or salt thereof) and elemental sulfur, the mixing being carried out at a temperature not greater than 95° C. and in the absence of any added liquid phase for a time effective to produce the organopolysulfide and/or salt thereof. In the context of the present invention, "in the absence of any added liquid phase" means that the mixing is conducted without any additional component, such as a solvent, being added in an amount sufficient to form a discrete liquid phase (e.g., a solution within which at least a portion of one or more of the reactants is dissolved). Minor or trace amounts of solvent or other compounds which are liquid at the mixing temperature may be present, however. Additionally, it is possible that upon mixing the initially solid reactants interact to form a liquid phase, but such a liquid phase would not be regarded as an added liquid phase within the context of the present invention.

In one embodiment, the organopolysulfide or salt thereof may correspond to general formula (I):

$$R—[—S_n\text{-M}]_p \qquad (I)$$

wherein n is an integer greater than 1, p is an integer of at least 1, R is an organic moiety containing from 1 to 25 carbon atoms and optionally also containing one or more hydrogen atoms and/or one or more heteroatoms (including heteroatoms which constitute part of functional groups), and M is an element or moiety carrying a formal positive charge (with the terminal S atom of the polysulfide chain $—S_n—$ carrying a formal negative charge);
and wherein the organomonosulfide or salt thereof corresponds to general formula (II):

$$R—[—S\text{-M}]_p \qquad (II)$$

wherein R, p and M have the same meaning as in general formula (I).

R may, in one embodiment, contain at least one heteroatom selected from the group consisting of N, O, S, Se, P and halides. The value of p, in various embodiments of the invention, may be 1, 2 or 3 or even greater than 3. M may, in various aspects of the invention, be selected from the group consisting of H, metals (e.g., Li, Na, K, ½ Ca), phosphonium, (e.g., quaternary phosphonium) and ammonium (e.g., quaternary ammonium). In a further aspect of the invention, the organomonosulfide corresponds to general formula (III):

$$R—S—R' \qquad (III)$$

wherein R and R' are the same as or different from each other and are each an organic moiety containing from 1 to 25 carbon atoms and optionally also containing one or more hydrogen atoms and/or one or more heteroatoms.

The mixing step of the method may, for example, be performed using at least one apparatus selected from the group consisting of mortars and pestles, dry blending devices, dry powder blenders, horizontal dry powder mixers, rotary batch mixers, ribbon blenders, paddle blenders, tumble blenders, vertical blenders, drum blenders, ball mills, rod mills, grinding rolls, buhrstone mills, stirred mills, jet mills, vibratory mills, hammer mills, disc mills, random orbit mixer mills, attrition mills, small media mills, agitated media mills and stirred media mills. The mixing may comprise grinding or milling the reactants (the organomonosulfide or salt thereof and elemental sulfur). The mixing may be performed in the absence of solvent, in the absence of catalyst, or in the absence of both solvent and catalyst. The mixing may be carried out at a temperature of 0° C. to 95° C., according to one aspect of the invention.

In certain embodiments, the method may additionally produce a co-product which is an inorganic polysulfide salt.

Also provided by the present invention is an organopolysulfide or salt thereof obtained by the method(s) described herein. These compositions may in turn be a component of a larger system, e.g., an electrochemical cell or battery where the compositions prepared by the methods described herein are used as one of the components of an electrode or as a component of any electrolyte.

DETAILED DESCRIPTION OF CERTAIN EMBODIMENTS OF THE INVENTION

In accordance with one embodiment of the invention, an organomonosulfide and/or a salt of an organomonosulfide is reacted with elemental sulfur to form an organopolysulfide salt. Combinations of different organomonosulfides, different organomonosulfide salts, or combinations of organomonosulfides and organomonosulfide salts may be so reacted with elemental sulfur. The reaction is achieved by mixing of the aforementioned starting materials at a temperature not greater than 95° C. and in the absence of any added liquid phase for a time effective to produce the organopolysulfide or salt thereof. This desired reaction may be achieved by mixing the reactants together under conditions such that at least the elemental sulfur is in the solid state prior to such mixing. In another embodiment, all the reactants are in the solid state prior to mixing. For example, the reaction may be carried out in the absence of any solvent capable of dissolving any reactant and at a temperature below the melting points of the reactants. In another embodiment, the mixing is carried out in the absence of any solvent capable of dissolving the elemental sulfur and at a temperature below the melting point of elemental sulfur (which is about 95° C.).

It will be recognized by those skilled in the art that intimate contact between solid phases of dissimilar compositions or surface energies can result in depression of the melting point of one or more of the solid phases. This intimate contact and resulting melting point depression could result in the formation of a liquid phase as a result of the mixing of the solid feedstocks. However, such a liquid phase would not be considered an added liquid phase, such as a solution formed by including a solvent capable of solubilizing one or both of the starting materials. Thus, the subjects of this invention refer to materials that are in a solid state prior to mixing, whether or not a liquid phase is formed as a result of mixing and intimately contacting the starting materials.

The selection of the starting organomonosulfide (or salt thereof) will be based upon the structure of the organopolysulfide (or salt thereof) that is desired as the product, since the organic moiety(ies) and "cationic" portion(s) of the organopolysulfide salt obtained will generally correspond to those present in the organomonosulfide or organomonosulfide salt reactant. That is, the organomonosulfide (or salt thereof) will typically contribute the organic moiety(ies) and "cationic" portion(s) of the organopolysulfide (or organopolysulfide salt) reaction product (the term "cationic" refers to the portion of the compound associated with a terminal sulfur atom which bears a formal positive charge, such as H⁺, Li⁺, Na⁺, Ca⁺², K⁺, other metal cations, quaternary ammonium, quaternary phosphonium, etc.). The following equation may be used to illustrate the overall reaction which takes place according to one aspect of the present invention:

[R—S]⁻[M]⁺+S$_q$→[R—S$_n$]⁻[M]⁺+M$_2$S$_m$, with m+n=q+1

The value of n may be any integer greater than 1, but typically is within the range of 2 to 30 (e.g., 2 to 10). Moreover, species with various values of n and m may be formed and coexist as the products of this reaction. M can be H, Li, Na, Ca, K, other metals, ammonium (including quaternary ammonium), and/or phosphonium (including quaternary phosphonium), for example. As shown in this exemplary reaction scheme, an inorganic polysulfide salt may be produced as a co-product in addition to the organopolysulfide salt. The reaction product obtained may include a mixture of organopolysulfides or salts thereof which differ with respect to the value of n. The reaction product could also contain some amount of unreacted organomonosulfide (or organomonosulfide salt) and/or elemental sulfur, depending upon the initial stoichiometry of the reactants and the mixing conditions employed.

The starting organomonosulfide (or salt thereof) in one embodiment of the invention contains an organic moiety and at least one monosulfide group —S-M attached to the organic moiety (that is, the sulfur atom of the —S-M group is bonded to a carbon atom of the organic moiety). In another embodiment of the invention, the starting organomonosulfide is a thioether, wherein two organic moieties are covalently bonded to a single sulfur atom (e.g., the organomonosulfide may correspond to the structure R—S—R', wherein R and R' are each an organic moiety, which may be the same as or different from each other).

The type of organic moiety or organic moieties present in the organomonosulfide (or salt thereof) is/are not limited and may be any organic group containing one or more carbon atoms as well as possibly one or more hydrogen atoms and one or more heteroatoms such as N, O, S, Se, P, halides and combinations thereof. For example, the organic moiety may contain from 1 to 30 or from 2 to 20 carbon atoms.

In one aspect of the invention, the organomonosulfide (or salt thereof) corresponds to the general formula (II):

R—[S-M]$_p$     (II)

In various embodiments of the invention, p is an integer of at least 1 (e.g., 1, 2, 3, 4, etc.), R is an organic moiety containing from 1 to 25 carbon atoms and optionally also containing one or more hydrogen atoms and/or one or more heteroatoms, and M is an element or moiety carrying a formal positive charge (with the S atom carrying a formal negative charge). The valency of R will be dependent upon the value of p. For example, where p=1, R is monovalent, such as an alkyl group; where p=2, R is divalent, such as an alkylene group. The heteroatoms optionally present in R may be, for example, N, O, S, Se, P, halide or the like or combinations thereof.

The group R in formula (II) (and in corresponding formula (I)) will be described below; the group R will be indicated by the name of a monovalent group to which one sulfur atom is bonded. In formula (II), R may represent an aliphatic hydrocarbon group that optionally has at least one substituent, an alicyclic hydrocarbon group that optionally has at least one substituent, an aromatic hydrocarbon group that optionally has at least one substituent, a heterocyclic group that optionally has at least one substituent, or an oxyalkylene-containing group. The term "aliphatic hydrocarbon group" encompasses an alkyl group, an alkenyl group and an alkynyl group.

Examples of an "alkyl group" include a methyl group, an ethyl group, an n-propyl group, an i-propyl group, an n-butyl group, an s-butyl group, an i-butyl group, a t-butyl group, an n-pentyl group, an n-hexyl group, a nonyl group, an i-nonyl group, a decyl group, a lauryl group, a tridecyl group, a myristyl group, a pentadecyl group, a palmityl group, a heptadecyl group, and a stearyl group. A C$_6$-C$_{25}$ alkyl group may be used, for example.

Examples of an "alkenyl group" include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a heptenyl group, an octenyl group, a decenyl group, a pentadecenyl group, an eicosenyl group, and a tricosenyl group. A $C_6$-$C_{25}$ alkenyl group may be used.

Examples of an "alkynyl group" include an ethynyl group, a 1-propynyl group, a 2-propynyl group, a 1-butynyl group, a 2-butynyl group, a 3-butynyl group, a 1-methyl-2-propynyl group, a 2-methyl-2-propynyl group, a 1-pentynyl group, a 2-pentynyl group, a 3-pentynyl group, a 4-pentynyl group, a 1-methyl-2-butynyl group, a 2-methyl-2-butynyl group, a 1-hexynyl group, a 2-hexynyl group, a 3-hexynyl group, a 4-hexynyl group, a 5-hexynyl group, a 1-heptynyl group, a 1-octynyl group, a 1-decynyl group, a 1-pentadecynyl group, a 1-eicosynyl group, and a 1-tricosynyl group. A $C_6$-$C_{25}$ alkynyl group may be used, for example.

The term "alicyclic hydrocarbon group" refers to a monocyclic or polycyclic alkyl group, alkenyl group, and the like, and examples thereof include a cyclopropyl group, a cyclobutyl group, a cyclopentyl group, a cyclohexyl group, a cycloheptyl group, a cyclooctyl group, a cyclododecyl group, a bicyclooctyl group, a bicycloheptyl group, a norbornyl group, an adamantyl group, a 2-cyclopropenyl group, a 2-cyclopentenyl group, and a 4-cyclohexenyl group. A $C_3$-$C_8$ cycloalkyl group may be used, for example.

The term "aromatic hydrocarbon group" means a monocyclic or polycyclic aryl group. Here, in the case of a polycyclic aryl group, the term aromatic hydrocarbon group also encompasses a partially saturated group in addition to a fully unsaturated group. Examples thereof include a phenyl group, a naphthyl group, an azulenyl group, an indenyl group, an indanyl group, and a tetralinyl group. A $C_6$-$C_{10}$ aryl group may be used.

The term "heterocyclic group" means a 5- to 7-membered aromatic heterocycle, saturated heterocycle or unsaturated heterocycle having 1 to 4 nitrogen atoms, oxygen atoms or sulfur atoms as a hetero atom(s), or a condensed heterocycle in which any of these heterocycles is condensed with another carbocyclic (e.g., benzene) or heterocyclic ring. Examples thereof include a furan-2-yl group, a furan-3-yl group, a thiophen-2-yl group, a thiophen-3-yl group, a pyrrol-1-yl group, a pyrrol-2-yl group, a pyridin-2-yl group, a pyridin-3-yl group, a pyridin-4-yl group, a pyrazin-2-yl group, a pyrazin-3-yl group, a pyrimidin-2-yl group, a pyrimidin-4-yl group, a pyridazin-3-yl group, a pyridazin-4-yl group, a 1,3-benzodioxol-4-yl group, a 1,3-benzodioxol-5-yl group, a 1,4-benzodioxan-5-yl group, a 1,4-benzodioxan-6-yl group, a 3,4-dihydro-2H-1,5-benzodioxepin-6-yl group, a 3,4-dihydro-2H-1,5-benzodioxepin-7-yl group, a 2,3-dihydrobenzofuran-4-yl group, a 2,3-dihydrobenzofuran-5-yl group, a 2,3-dihydrobenzofuran-6-yl group, a 2,3-dihydrobenzofuran-7-yl group, a benzofuran-2-yl group, a benzofuran-3-yl group, a benzothiophen-2-yl group, a benzothiophen-3-yl group, a quinoxalin-2-yl group, a quinoxalin-5-yl group, an indol-1-yl group, an indol-2-yl group, an isoindol-1-yl group, an isoindol-2-yl group, an isobenzofuran-1-yl group, an isobenzofuran-4-yl group, a chromen-2-yl group, a chromen-3-yl group, an imidazol-1-yl group, an imidazol-2-yl group, an imidazol-4-yl group, a pyrazol-1-yl group, a pyrazol-3-yl group, a thiazol-2-yl group, a thiazol-4-yl group, an oxazol-2-yl group, an oxazol-4-yl group, an isoxazol-3-yl group, an isoxazol-4-yl group, a pyrrolidin-2-yl group, a pyrrolidin-3-yl group, a benzoimidazol-1-yl group, a benzoimidazol-2-yl group, a benzothiazol-2-yl group, a benzothiazol-4-yl group, a benzoxazol-2-yl group, a benzoxazol-4-yl group, a quinolin-2-yl group, a quinolin-3-yl group, an isoquinolin-1-yl group, an isoquinolin-3-yl group, a 1,3,4-thiadiazol-2-yl group, a 1,2,3-triazol-1-yl group, a 1,2,3-triazol-4-yl group, a tetrazol-1-yl group, a tetrazol-2-yl group, an indolin-4-yl group, an indolin-5-yl group, a morpholin-4-yl group, a piperazin-2-yl group, a piperidin-2-yl group, a 1,2,3,4-tetrahydroquinolin-5-yl group, a 1,2,3,4-tetrahydroquinolin-6-yl group, a 1,2,3,4-tetrahydroisoquinolin-5-yl group, and a 1,2,3,4-tetrahydroisoquinolin-6-yl group. In one embodiment, R is a 1,3,4-thiadiazole group.

The term "ether-containing group" means an organic moiety containing one or more ether linkages, such as, for example, an oxyalkylene-containing group. An oxyalkylene-containing group may be a group that contains at least one moiety having general structure —O—$(CH_2)_o$— wherein o is an integer of at least 1 (e.g., 1, 2, 3, 4, etc.) and one or more of the hydrogen atoms in the $CH_2$ moieties may be replaced with a substituent such as an alkyl group (e.g., methyl or ethyl), aryl group or heterocyclic moiety. As an example, R in one embodiment of the invention is a divalent oxyalkylene-containing moiety, such as —$CH_2CH_2OCH_2CH_2OCH_2CH_2$—.

The identity of M in formulas (I) and (II) is not believed to be critical and may be hydrogen or any cationic species capable of forming a salt with the anionic terminus of the organosulfide or organopolysulfide (—$S^-$). For example, M may be an alkali metal cation (e.g., $Li^+$, $Na^+$, $K^+$), alkaline earth metal cation (e.g., ½ $Ca^{2+}$), other metal cation, ammonium moiety or phosphonium moiety. The ammonium moiety may be a quaternary ammonium moiety. The phosphonium moiety may be a quarternary phosphonium moiety. For example, M may be N(R')(R")(R"')(R"") or P(R')(R")(R"')(R""), wherein R', R", and R"" are the same or different and are H or an organic group such as an alkyl group or an aromatic group).

In the embodiment of the invention in which the starting organomonosulfide correspond s to the structure R—S—R' (III), wherein R and R' are each an organic moiety (which may be the same as or different from each other), the overall reaction with elemental sulfur may be represented as follows (illustrating the situation where the elemental sulfur is completely reacted):

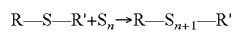

R and R' may be any of the organic moieties mentioned above in connection with the description of group R in formulae (I) and (II). Thus, R and R' may independently represent an aliphatic hydrocarbon group that optionally has at least one substituent, an alicyclic hydrocarbon group that optionally has a substituent, an aromatic hydrocarbon group that optionally has at least one substituent, a heterocyclic group that optionally has at least one substituent, or an oxyalkylene-containing group.

Illustrative examples of suitable organomonosulfide salts useful as starting materials in the process of the present invention include $C_{12}H_{25}SLi$ (lithium n-dodecylpolythiolate), $CH_3OCH_2CH_2SLi$, $LiSCH_2CH_2OCH_2CH_2OCH_2CH_2SLi$ (lithium 3,6-dioxaoctane-1,8-polythiolate), $C_6H_5SNa$ and 2,5-dimercapto-1,3,4-thiadiazole dipotassium salt.

Elemental sulfur is readily available from numerous commercial sources and generally may be employed without any preliminary purification or processing being necessary. It is also recognized that elemental sulfur may exist in various allotropic forms and as any number of homologous species, e.g., $S_6$, $S_8$, $S_{12}$, homopolymeric species $S_z$, etc. Any of such homologs and allotropes or mixtures thereof may be used as the elemental sulfur in accordance with the present invention.

The relative amounts of organomonosulfide (or organomonosulfide salt) and elemental sulfur used may be varied as may be desired to order to achieve a particular degree of oligomerization in the polysulfide portion (—$S_n$—) of the reaction product. Generally speaking, the value of n will increase as the molar amount of elemental sulfur is increased relative to the molar amount of organomonosulfide or organomonosulfide salt. For example, the amounts of organomonosulfide (or salt thereof) and the elemental sulfur used as reactants may be selected to provide a molar ratio of S (the molar amount of sulfur present in the elemental sulfur) to organomonosulfide (or organomonosulfide salt) of from 1:1 to 50:1.

Generally speaking, it will be advantageous to mix the organomonosulfide (or salt thereof) and the elemental sulfur under conditions effectively so as to intimately combine the two components. As the reaction requires intimate contact of the initially solid particles, it is also advantageous, but not required, that the solid reactants may be utilized in fine particulate form; if the reactants are not in such form to begin with, grinding and/or milling techniques may be employed so as to reduce the initial particle size. Grinding and/or milling after mixing of the reactants also may help to facilitate the desired reaction of the organomonosulfide (or salt thereof) and elemental sulfur.

The process of the invention may be carried out using any apparatus or technique known in the art to be suitable for intimately mixing, contacting and communiting solid substances, particularly solid substances that are in particulate form. For example, the organomonosulfide (or salt thereof) and elemental sulfur may be mixed using a grinding or mixing apparatus such as a simple mortar and pestle, a dry blending device, a dry powder blender, a horizontal dry powder mixer, a rotary batch mixer, a ribbon blender, a paddle blender, a tumble blender, a vertical blender, a drum blender, a ball mill (including a planetary ball mill), a ribbon blender, a rotary kiln, a jet mill, a rod mill, grinding rolls (sometimes also referred to as roller presses or roller mills, including high pressure grinding rolls), a buhrstone mill, a stirred mill, a vibratory mill (including a high amplitude vibration mill and a low amplitude vibration mill), a hammer mill, a disc mill, a random orbit mixer mill, an attrition mill, a small media mill, an agitated media mill and a stirred media mill. Combinations of such apparatus may also be used; for example, organomonosulfide (or salt thereof) and elemental sulfur may first be subjected to mixing in one type of grinding or mixing apparatus to obtain a mixture that is then subjected to further processing in a second type of grinding or mixing apparatus.

The temperature during such mixing step may be controlled so that at least the elemental sulfur remains in solid state form. Mixing temperatures of from 0° C. to 95° C. may be employed, for example. Typically, mixing temperatures of around room temperature (i.e., about 15° C. to about 35° C.) have been found to be sufficient.

Once the desired extent of reaction has been achieved (which typically takes from 0.2 to 5 hours), mixing may be discontinued and the resulting reaction product containing the organopolysulfide or organopolysulfide salt recovered and, optionally, subjected to further processing and/or purification steps as may be desired. The organopolysulfide or organopolysulfide salt thereby obtained may be utilized in any of the end-use applications known in the art for such substances, including, for example, as components of metal-sulfur batteries as described in WO 2013/155038.

Aspects of the present invention include:

A method of producing an organopolysulfide or salt thereof, wherein the method comprises a step of mixing an organomonosulfide or salt thereof and elemental sulfur, wherein the mixing is carried out at a temperature not greater than 95° C. and in the absence of any added liquid phase for a time effective to produce the organopolysulfide or salt thereof.

The method, wherein the organopolysulfide or salt thereof corresponds to general formula (I):

$$R\text{—}[S_n\text{-}M]_p \quad (I)$$

wherein n is an integer greater than 1, p is an integer of at least 1, R is an organic moiety containing from 1 to 25 carbon atoms and optionally also containing one or more hydrogen atoms and/or one or more heteroatoms, and M is an element or moiety carrying a formal positive charge;

and wherein the organomonosulfide or salt thereof corresponds to general formula (II):

$$R\text{—}[S\text{-}M]_p \quad (II)$$

wherein R, M and p have the same meaning as in general formula (I).

The method, wherein p is an integer of from 1 to 3.
The method, wherein n is an integer of from 2 to 30.
The method, wherein R is a hydrocarbon moiety optionally containing one or more heteroatoms.
The method, wherein R is a hydrocarbon moiety optionally containing one or more heteroatoms and contains at least one heteroatom selected from the group consisting of N, O, S, Se, P and halides.
The method, wherein M is selected from the group consisting of H, Li, Na, K, ½ Ca, metals, phosphonium moieties, and ammonium moieties.
The method of claim 1, wherein the organomonosulfide corresponds to general formula (III):

$$R\text{—}S\text{—}R' \quad (III)$$

wherein R and R' are the same as or different from each other and are each an organic moiety containing from 1 to 25 carbon atoms and optionally also containing one or more hydrogen atoms and/or one or more heteroatoms.

The method, wherein the mixing is performed using at least one apparatus selected from the group consisting of mortars and pestles, ball mills, ribbon blenders, rotary kilns, jet mills, rod mills, grinding rolls, buhrstone mills, stirred mills, vibratory mills, hammer mills, disc mills, random orbit mixer mills, attrition mills, small media mills, agitated media mills and stirred media mills.

The method, wherein the mixing comprises grinding or milling the organomonosulfide or salt thereof and elemental sulfur.

The method, wherein the method additionally produces a co-product which is an inorganic polysulfide salt.

The method, wherein the mixing is performed in the absence of catalyst.

The method, wherein p is 1, 2 or 3.
The method, wherein the mixing is carried out at a temperature of from 0° C. to 95° C.
The method, wherein R is a $C_6$-$C_{25}$ hydrocarbon group.
The method, wherein R is an oxyalkylene-containing group.
The method, wherein R is a divalent oxyethylene-containing group.
The method, wherein M is an alkali metal.
The method, wherein M is Li.

The method, wherein both the organomonosulfide or salt thereof and the elemental sulfur are in the solid state prior to mixing.

An organopolysulfide or salt thereof obtained by the method of any combination of any of the above aspects of the invention.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

In a glovebox, 0.1000 g of $C_{12}H_{25}SLi$ was weighed into a 20 mL scintillation vial. 0.0462 g elemental sulfur was then added to the same vial. A stir bar was placed in the vial and the vial was capped. The closed container was placed on a magnetic stirrer. After 2 h, the color of the mixed material had changed to bright canary yellow.

Example 2

In a glovebox, 0.1000 g of Li—S—$C_2H_4$—O—$C_2H_4$—O—$C_2H_4$—S—Li was weighed into a 20 mL scintillation vial. 0.1055 g elemental sulfur was then added to the same vial. A stir bar was placed in the vial and the vial was capped. The closed container was placed on a magnetic stirrer. After 2 h, the color of the mixed material had changed to bright canary yellow.

Example 3

In a glovebox, 5.000 g of Li—S—$C_2H_4$—O—$C_2H_4$—O—$C_2H_4$—S—Li was weighed into a 100 mL flask. 4.94 g elemental sulfur was then added to the same flask. A stir bar was placed in the flask and the flask was capped. The closed container was placed on a magnetic stirrer. After 2 h, the color of the mixed material had changed to yellow.

Example 4

In a glovebox, 1.000 g of $C_6H_5SNa$ was weighed into a 20 mL scintillation vial. 0.7264 g elemental sulfur was then added to the same vial. A stir bar was placed in the vial and the vial was capped. The closed container was placed on a magnetic stirrer. After 1 h, the color of the mixed material had changed to yellow.

Example 5

In a glovebox, 1.000 g of 2,5-dimercapto-1,3,4-thiadiazole dipotassium salt was weighed into a 20 mL scintillation vial. 0.4239 g elemental sulfur was then added to the same vial. A stir bar was placed in the vial and the vial was capped. The closed container was placed on a magnetic stirrer. After 1 h, the color of the mixed material had changed to yellow.

What is claimed is:

1. A method of producing an organopolysulfide or salt thereof, wherein the method comprises a step of mixing an organomonosulfide or salt thereof and elemental sulfur, wherein the mixing is carried out at a temperature not greater than 95° C. and in the absence of any added liquid phase for a time effective to produce the organopolysulfide or salt thereof and wherein the mixing is performed in the absence of catalyst.

2. The method of claim 1, wherein the organopolysulfide or salt thereof corresponds to general formula (I):

$$R-[S_n-M]_p \qquad (I)$$

wherein n is an integer greater than 1, p is an integer of at least 1, R is an organic moiety containing from 1 to 25 carbon atoms and optionally also containing one or more hydrogen atoms and/or one or more heteroatoms, and M is an element or moiety carrying a formal positive charge;

and wherein the organomonosulfide or salt thereof corresponds to general formula (II):

$$R-[S-M]_p \qquad (II)$$

wherein R, M and p have the same meaning as in general formula (I).

3. The method of claim 2, wherein p is an integer of from 1 to 3.

4. The method of claim 2, wherein n is an integer of from 2 to 30.

5. The method of claim 2, wherein R is a hydrocarbon moiety optionally containing one or more heteroatoms.

6. The method of claim 5, wherein R contains at least one heteroatom selected from the group consisting of N, O, S, Se, P and halides.

7. The method of claim 2, wherein M is selected from the group consisting of H, Li, Na, K, ½ Ca, metals, phosphonium moieties, and ammonium moieties.

8. The method of claim 1, wherein the organomonosulfide corresponds to general formula (III):

$$R-S-R' \qquad (III)$$

wherein R and R' are the same as or different from each other and are each an organic moiety containing from 1 to 25 carbon atoms and optionally also containing one or more hydrogen atoms and/or one or more heteroatoms.

9. The method of claim 1, wherein the mixing is performed using at least one apparatus selected from the group consisting of mortars and pestles, ball mills, ribbon blenders, rotary kilns, jet mills, rod mills, grinding rolls, buhrstone mills, stirred mills, vibratory mills, hammer mills, disc mills, random orbit mixer mills, attrition mills, small media mills, agitated media mills and stirred media mills.

10. The method of claim 1, wherein the mixing comprises grinding or milling the organomonosulfide or salt thereof and elemental sulfur.

11. The method of claim 1, wherein the method additionally produces a co-product which is an inorganic polysulfide salt.

12. The method of claim 2, wherein p is 1, 2 or 3.

13. The method of claim 1, wherein the mixing is carried out at a temperature of from 0° C. to 95° C.

14. The method of claim 2, wherein R is a C6-C25 hydrocarbon group.

15. The method of claim 2, wherein R is an oxyalkylene-containing group.

16. The method of claim 2, wherein R is a divalent oxyethylene-containing group.

17. The method of claim 2, wherein M is an alkali metal.

18. The method of claim 2, wherein M is Li.

19. The method of claim 1, wherein both the organomonosulfide or salt thereof and the elemental sulfur are in the solid state prior to mixing.

\* \* \* \* \*